US008828546B2

(12) United States Patent
Dias et al.

(10) Patent No.: US 8,828,546 B2
(45) Date of Patent: *Sep. 9, 2014

(54) COATED MEDICAL DEVICE

(75) Inventors: Aylvin Jorge Angelo Athanasius Dias, Maastricht (NL); Edith Elisabeth M. Van Den Bosch, Riemst (BE); Peter Bruin, Veldhoven (NL); Marnix Rooijmans, Born (NL); Rudolfus Antonius Theodorus Maria Van Benthem, Limbricht (NL)

(73) Assignee: DSM IP Assets B.V., Heerlen (NL)

( * ) Notice: Subject to any disclaimer, the term of this patent is extended or adjusted under 35 U.S.C. 154(b) by 996 days.

This patent is subject to a terminal disclaimer.

(21) Appl. No.: 12/440,532

(22) PCT Filed: Sep. 13, 2007

(86) PCT No.: PCT/EP2007/007984
§ 371 (c)(1),
(2), (4) Date: Jan. 4, 2010

(87) PCT Pub. No.: WO2008/031595
PCT Pub. Date: Mar. 20, 2008

(65) Prior Publication Data
US 2010/0114042 A1 May 6, 2010

(30) Foreign Application Priority Data

Sep. 13, 2006 (EP) .................................... 06019148
May 15, 2007 (EP) .................................... 07009702
May 15, 2007 (EP) .................................... 07009703

(51) Int. Cl.
A61M 25/00 (2006.01)
B32B 27/08 (2006.01)
B32B 27/26 (2006.01)

(52) U.S. Cl.
USPC .......... 428/411.1; 428/522; 604/523

(58) Field of Classification Search
None
See application file for complete search history.

(56) References Cited

U.S. PATENT DOCUMENTS

| 4,105,519 | A | 8/1978 | Pennewiss et al. |
| 4,111,922 | A | 9/1978 | Beede et al. |
| 4,117,184 | A | 9/1978 | Erickson et al. |
| 4,272,620 | A | 6/1981 | Ichimura |
| 4,612,336 | A | 9/1986 | Yada et al. |
| 4,818,325 | A * | 4/1989 | Hiraiwa et al. ............ 156/315 |
| 4,874,822 | A * | 10/1989 | Rasmussen et al. ......... 525/279 |
| 5,005,287 | A | 4/1991 | Ritter |
| 5,008,301 | A * | 4/1991 | Dennis et al. ................. 522/13 |
| 5,077,352 | A | 12/1991 | Elton |
| 5,084,315 | A | 1/1992 | Karimi et al. |
| 5,091,205 | A | 2/1992 | Fan |
| 5,135,516 | A | 8/1992 | Sahatjian et al. |
| 5,317,063 | A | 5/1994 | Komatsu et al. |
| 5,317,080 | A | 5/1994 | Arimatsu et al. |
| 5,670,557 | A | 9/1997 | Dietz |
| 5,700,559 | A | 12/1997 | Sheu et al. |
| 5,702,754 | A | 12/1997 | Zhong |
| 5,756,144 | A | 5/1998 | Wolff et al. |
| 5,804,318 | A | 9/1998 | Pinchuk et al. |
| 5,985,990 | A | 11/1999 | Kantner et al. |
| 5,994,419 | A | 11/1999 | Collette et al. |
| 6,048,620 | A | 4/2000 | Zhong |
| 6,110,451 | A | 8/2000 | Matz et al. |
| 6,120,904 | A | 9/2000 | Hostettler et al. |
| 6,221,425 | B1 * | 4/2001 | Michal et al. ............. 427/2.25 |
| 6,238,799 | B1 | 5/2001 | Opolski |
| 6,310,116 | B1 | 10/2001 | Yasuda et al. |
| 6,565,981 | B1 | 5/2003 | Messner et al. |
| 6,589,665 | B2 | 7/2003 | Chabrecek et al. |
| 6,673,053 | B2 | 1/2004 | Wang et al. |
| 6,709,706 | B2 | 3/2004 | Zhong et al. |
| 6,720,130 | B1 * | 4/2004 | Zhong et al. ............. 430/273.1 |
| 6,835,783 | B1 | 12/2004 | Gartner et al. |
| 6,849,685 | B2 | 2/2005 | Soarens et al. |
| 6,887,961 | B2 | 5/2005 | Soarens et al. |
| 7,264,859 | B2 | 9/2007 | Rouns et al. |
| 7,544,381 | B2 | 6/2009 | Kangas |
| 8,133,580 | B2 | 3/2012 | Dias et al. |
| 2001/0011165 | A1 | 8/2001 | Engelson et al. |
| 2001/0027299 | A1 | 10/2001 | Yang et al. |
| 2002/0002353 | A1 | 1/2002 | Michal et al. |
| 2002/0013549 | A1 | 1/2002 | Zhong et al. |
| 2003/0013615 | A1 | 1/2003 | Levy |
| 2003/0096131 | A1 | 5/2003 | Beavers et al. |
| 2003/0218130 | A1 | 11/2003 | Boschetti et al. |
| 2004/0019168 | A1 | 1/2004 | Soarens et al. |

(Continued)

FOREIGN PATENT DOCUMENTS

| EP | 0 289 996 | 11/1988 |
| EP | 0 405 464 | 1/1991 |

(Continued)

OTHER PUBLICATIONS

International Search Report for PCT/EP2007/007984, mailed Apr. 11, 2008.
Written Opinion of the International Searching Authority for PCT/EP2007/007984, mailed Apr. 11, 2008.
Alt, V. et al., "Plasma Polymer Coating with High-Porosity Silver for Antimicrobial Protection of Osteosynthetic Devices," Osteosynthese International 2005—Kongress, Oral Presentation, No. 075, Sep. 15, 2005, 1 page.
Asha, S.K. et al., "Synthesis and Curing Studies of PPG based Telechelic Urethane Methacrylic Macromonomers," European Polymer Journal, vol. 41, No. 1, Jan. 2005, pp. 23-33.

(Continued)

Primary Examiner — Ramsey Zacharia
(74) Attorney, Agent, or Firm — Nixon & Vanderhye P.C.

(57) ABSTRACT

The invention relates to an article comprising a coating, which coating comprises at least two layers, of which the inner layer is a primer layer, comprising a supporting network comprising a supporting polymer, and the outer layer is a functional layer comprising a multifunctional polymerizable compound.

21 Claims, 2 Drawing Sheets

(56) References Cited

U.S. PATENT DOCUMENTS

| | | |
|---|---|---|
| 2004/0043688 A1 | 3/2004 | Soarens et al. |
| 2004/0110861 A1 | 6/2004 | Shorbu et al. |
| 2004/0125338 A1 | 7/2004 | Phelan et al. |
| 2004/0135967 A1 | 7/2004 | Carney et al. |
| 2004/0143180 A1 | 7/2004 | Zhong et al. |
| 2004/0161444 A1 | 8/2004 | Song et al. |
| 2005/0054774 A1 | 3/2005 | Kangas |
| 2005/0080157 A1 | 4/2005 | Wagener et al. |
| 2005/0100580 A1 | 5/2005 | Osborne et al. |
| 2005/0137582 A1 | 6/2005 | Kull-Osterlin et al. |
| 2005/0170071 A1 | 8/2005 | Eramo |
| 2005/0191430 A1 | 9/2005 | Rubner et al. |
| 2006/0240060 A1 | 10/2006 | Bavaro |
| 2007/0167735 A1 | 7/2007 | Zhong et al. |
| 2008/0292776 A1 | 11/2008 | Dias et al. |
| 2008/0306455 A1 | 12/2008 | Dias et al. |
| 2009/0169715 A1 | 7/2009 | Dias et al. |
| 2010/0113871 A1 | 5/2010 | Dias et al. |
| 2010/0198168 A1 | 8/2010 | Rooijmans |
| 2011/0046255 A1 | 2/2011 | Rooijmans |
| 2011/0059874 A1 | 3/2011 | Rooijmans et al. |

FOREIGN PATENT DOCUMENTS

| | | |
|---|---|---|
| EP | 0 480 809 | 4/1992 |
| EP | 1 065 738 | 1/2001 |
| EP | 1 621 217 | 2/2006 |
| EP | 1 776 968 | 4/2007 |
| JP | 3-250013 | 11/1991 |
| JP | H04-144567 | 5/1992 |
| JP | H06-039347 | 2/1994 |
| JP | H10-211273 | 8/1998 |
| JP | H10-277144 | 10/1998 |
| JP | H11-172149 | 6/1999 |
| JP | 2001-000531 | 1/2001 |
| JP | 2005-508398 | 3/2005 |
| JP | 2006-513745 | 4/2006 |
| WO | WO 96/28762 | 9/1996 |
| WO | WO 97/17378 | 5/1997 |
| WO | WO 98/50461 | 11/1998 |
| WO | WO 98/58989 | 12/1998 |
| WO | WO 99/38546 | 8/1999 |
| WO | WO 01/51103 | 7/2001 |
| WO | 01/92584 | 12/2001 |
| WO | WO 01/92584 | 12/2001 |
| WO | 02/087734 | 11/2002 |
| WO | 03/094975 | 11/2003 |
| WO | WO 2004/056321 | 7/2004 |
| WO | WO 2004/056909 | 7/2004 |
| WO | WO 2004/060427 | 7/2004 |
| WO | WO 2004/091685 | 10/2004 |
| WO | 2005/025631 | 3/2005 |
| WO | WO 2006/042514 | 4/2006 |
| WO | 2006/056482 | 6/2006 |
| WO | WO 2006/056482 | 6/2006 |
| WO | WO 2006/081079 | 8/2006 |
| WO | WO 2007/065722 | 6/2007 |
| WO | WO 2008/012325 | 1/2008 |
| WO | WO 2008/031596 | 3/2008 |
| WO | WO 2008/071796 | 6/2008 |
| WO | WO 2008/104573 | 8/2008 |
| WO | WO 2011/157805 | 12/2011 |

OTHER PUBLICATIONS

Guggenbichler, J.P. et al., "A New Technology of Microdispersed Silver in Polyurethane Induces Antimicrobial Activity in Central Venous Catheters," Infection, vol. 27, Suppl. 1, pp. S16-S23, 1999.

Samuel, U. et al., "Prevention of Catheter-Related Infections: the Potential of a New Nano-Silver Impregnated Catheter," International Journal of Antimicrobial Agents, vol. 23, Suppl. 1, pp. S75-S78, Mar. 2004.

Database WPI Week 199517, Thomas Scientific, XP 002451204 & JP 07 053895, Feb. 28, 1995 Abstract.

International Search Report for PCT/EP2006/011902, dated Aug. 6, 2007.

Written Opinion of the International Searching Authority for PCT/EP2006/011902, dated Aug. 6, 2007.

International Search Report for PCT/EP2006/0111903, dated Aug. 8, 2007.

Written Opinion of the International Searching Authority for PCT/EP2006/011903, dated Aug. 8, 2007.

International Search Report for PCT/EP2006/011904, dated Mar. 16, 2007.

Written Opinion of the International Searching Authority for PCT/EP2006/011904, dated Mar. 16, 2007.

International Search Report for PCT/EP2007/007995, dated Feb. 27, 2008.

Written Opinion of the International Searching Authority for PCT/EP2007/007995, dated Feb. 27, 2008.

International Search Report for PCT/ EP2008/052396, mailed Feb. 16, 2009.

Written Opinion of the International Searching Authority for PCT/EP2008/052396, mailed Feb. 16, 2009.

International Search Report for PCT/EP2008/052397, mailed Jan. 13, 2009.

International Search Report for PCT/EP2009/032918, mailed Jun. 22, 2009.

Written Opinion of the International Searching Authority for PCT/EP2009/052918, mailed Jun. 22, 2009.

Japanese Patent Office, Notice of Reasons for Rejection, P2008-543747, Dispatch No. 004257 (Jan. 10, 2012) (English Translation).

Japanese Patent Office, Final Rejection, P2008-543747. Dispatch No. 472881 (Jul. 17, 2012) (English Translation).

U.S. Appl. No. 13/704,714, filed Dec. 17, 2012.

Walline et al, *Synthesis of a Thrombin Responsive Drug Delivery Coating for Cardiovascular Stents*, Polymer Preprints 2003, 44(1), 193-194.

U.S. Appl. No. 12/920,399, Official Action dated May 21, 2013.

JP Office Action mailed Aug. 6, 2013 with translation.

JP Office Action mailed Oct. 1, 2013 with translation.

U.S. Appl. No. 12/440,775, Office Action dated Apr. 10, 2014.

\* cited by examiner

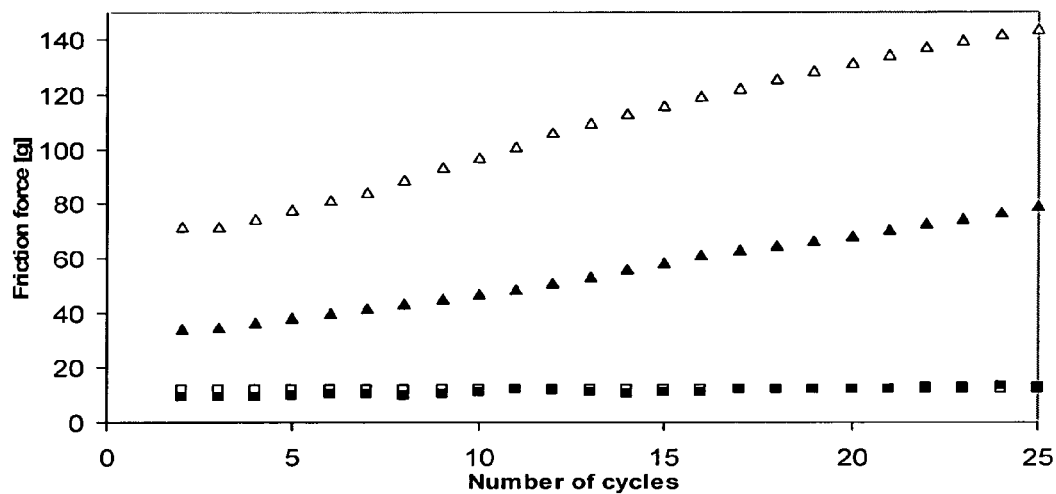
Figure 1 : Friction forces obtained for PVC tubing coated with primer layer and a functional layer with PEGDA, immersed in distilled water. The coating was prepared from a functional coating formulation incubated at 50°C for 0 (squares) and 2 (triangles) days. The closed and open squares/triangles represent the first and second test on the coatings, respectively

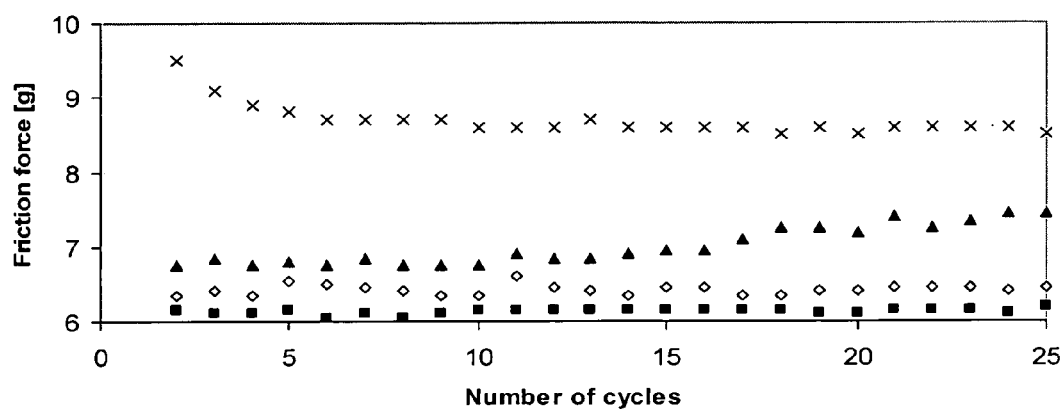
Figure 2 : Friction forces obtained for PVC tubing coated with primer layer and a functional layer without PEG(AM)$_2$ (x) and with PEG(AM)$_2$, immersed in distilled water. The coating containing PEG(AM)$_2$ was prepared from a functional coating formulation incubated at 50°C for 0 (◇), 2 (■) and 7 (▲) days.

COATED MEDICAL DEVICE

This application is the U.S. national phase of International Application No. PCT/EP2007/007984, filed 13 Sep. 2007, which designated the U.S. and claims priority to Europe Application Nos. 06019148.3 filed 13 Sep. 2006; 07009703, filed 15 May 2007 and 07009702.7, filed 15 May 2007, the entire contents of each of which are hereby incorporated by reference.

FIELD

This invention relates to an article comprising a coating, a primer coating formulation for providing an article with a primer layer, a functional coating formulation for providing an article with an outer layer, a coating system, a method of coating an article, a medical coating, a hydrophilic coating and a lubricious coating.

BACKGROUND

People have continually attempted to impart certain functional properties to a surface by applying coatings to it. Many medical devices, such as urinary and cardiovascular catheters, syringes, and membranes need to have a lubricant applied to the outer and/or inner surface to facilitate insertion into and removal from the body and/or to facilitate drainage of fluids from the body. Lubricious properties are also required so as to minimize soft tissue damage upon insertion or removal. Especially, for lubrication purposes, such medical devices may have a hydrophilic surface coating or layer which becomes lubricious and attains low-friction properties upon wetting, i.e. applying a wetting fluid for a certain time period prior to insertion of the device into the body of a patient. A hydrophilic surface coating or layer which becomes lubricious after wetting is hereinafter referred to as a hydrophilic coating. A coating obtained after wetting is hereinafter referred to as a lubricious coating.

Coating formulations for use in such lubricious coatings may comprise for example a multifunctional polymerizable compound, which is polymerized upon curing in the presence of an initiator and which provides improved robustness of the coating as well as a controllable network which will allow tuned release of for example metal ions and/or other antimicrobial agents, and also allow entrapment of for example extractables. Moreover a hydrophilic polymer may be present to provide a higher hydrophilicity of the coating, and/or to provide an improved dry-out time. Preferably all the components of said coating formulations are sufficiently hydrophilic in order to obtain a homogeneous mixture of said components resulting in favorable coating performance.

In WO 2006/056482 A1 a hydrophilic coating is disclosed comprising a supporting polymer (polyethylene glycol diacrylate, PEG4000 diacrylate, number average molecular weight of the polyethylene glycol 4000 g/mol), a hydrophilic polymer (polyvinylpyrollidone, PVP) and an initiator.

SUMMARY

It is an object of the present invention to provide a novel article, comprising a coating which may be used as an alternative to a known article.

It is in particular an object to provide a novel article comprising a robust and consistent lubricious coating. This is particularly useful as the inventors have found that known coating formulations often results in coatings with inferior coating performance. Typically such coatings tend to degrade within a given time in a hydrated environment causing increase in extractables or leachables. Such extractables or leachables may comprise low molecular and/or polymeric compounds and/or particles which may be vital to the function of the coating and/or may have detrimental effects in the body fluid in which they are released. Degradation of said coatings typically results in loss of properties such as ability to hydrate and maintain hydration, loss of lubricious properties, loss of patient comfort, increased risk of infection due to the residue being left on the tissue surface, uncontrolled release and co-elution problems for biologically active components. Moreover, the lack of mechanical robustness, as demonstrated by the fact that parts of the coating are easily removed from the coated article upon rubbing, may result in undesired particle release in for example cardiovascular applications.

Degradation may also occur in the liquid state, i.e. prior to the preparation of the coating. This adversely affects the performance of the coating in terms of ability to coat the given surface, wetting and optical appearance. This limits the shelf life stability of the coating formulation and requires acceptable quality control prior to use in sensitive medical application. It is therefore also an object to provide coating formulations which are more stable in the liquid state.

It is further an object to provide a method for preparing a coated article.

One or more other objects that may be solved in accordance with the present invention will become apparent from the description, below.

BRIEF DESCRIPTION OF THE DRAWINGS

FIG. 1 is a graph of friction force (g) vs. number of cycles for PVC tubing coated with a primer layer and a functional layer; and FIG. 2 is a graph of friction force (g) vs. number of cycles for PVC tubing coated with a primer layer and a functional layer.

DETAILED DESCRIPTION

It has now been found possible to solve one or more objects by providing an article with a specific coating comprising a primer layer and a functional layer.

Accordingly, the present invention relates to an article—in particular a medical device, more in particular a catheter—comprising a coating, which coating comprises at least two layers, of which the inner layer is a primer layer, comprising a supporting network comprising a supporting polymer (a), and the outer layer is a functional layer comprising (A) at least one multifunctional polymerizable compound according to formula (1)

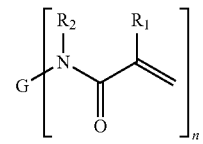

wherein G is a residue of a polyfunctional compound having at least n functional groups, wherein G is preferably hydrophilic, more preferably chosen from the group consisting of polyethers, polyesters, polyurethanes, polyepoxides, polyamides, polyacrylamides, poly(meth)acrylics, polyoxazolidones, polyvinyl alcohols, polyethylene imines, polypeptides and polysaccharides, such as cellulose or starch or any combination of the above, and wherein G is more preferably a polymer comprising at least one polyethyleneglycol or polypropylene glycol block; wherein each $R_1$ and each $R_2$ independently represents hydrogen or a group selected from substituted and unsubstituted hydrocarbons which optionally contain one or more heteroatoms, preferably hydrogen or a C1-C20 hydrocarbon, more preferably hydrogen or a C1-C20 alkyl; and wherein n is an integer having a value of at least 2, preferably 2-100, more preferably 2-8, in particular 2 or 3.

It has in particular been found that in accordance with the invention a coating is provided that is more robust and consistent, which is particularly apparent in a hydrated environment. Moreover, the coating may show a satisfactory or even advantageous adherence to the surface of the article, less visible cracks, and/or lubricity after wetting the coating with water.

Within the context of the invention "lubricious" is defined as having a slippery surface. A coating on the outer or inner surface of a medical device, such as a catheter, is considered lubricious if (when wetted) it can be inserted into the intended body part without leading to injuries and/or causing unacceptable levels of discomfort to the subject. In particular, a coating is considered lubricious if it has a friction as measured on a Harland FTS5000 Friction Tester (HFT) of 20 g or less at a clamp-force of 300 g, a pull speed of 1 cm/s and a temperature of 22° C. The protocol is as indicated in the Examples. The time that the hydrophilic coating stays lubricious upon applying a wetting fluid is herein further referred to as dry-out time.

The term "wetted" is generally known in the art and—in a broad sense—means "containing water". In particular the term is used herein to describe a coating that contains sufficient water to be lubricious. In terms of the water concentration, usually a wetted coating contains at least 10 wt % of water, based on the dry weight of the coating, preferably at least 50 wt %, based on the dry weight of the coating, more preferably at least 100 wt % based on the dry weight of the coating. For instance, in a particular embodiment of the invention a water uptake of about 300-500 wt % water is feasible. Examples of wetting fluids are treated or untreated water, water-containing mixtures with for example organic solvents or aqueous solutions comprising for example salts, proteins or polysaccharides. In particular a wetting fluid can be a body fluid.

Within the context of the invention the term polymer is used for a molecule comprising two or more repeating units. In particular it may be composed of two or more monomers which may be the same or different. As used herein, the term includes oligomers and prepolymers. Usually polymers have a number average weight (Mn) of about 500 g/mol or more, in particular of about 1000 g/mol or more, although the Mn may be lower in case the polymer is composed of relatively small monomeric units. Herein and hereinafter the Mn is defined as the Mn as determined by light scattering.

The primer layer generally contributes to the adherence of the functional layer, in particular if the surface of the article provided with the functional layer is more hydrophobic than the functional layer. Examples of suitable surfaces are for instance surfaces that consist of metals, polymers—especially plastics—and ceramics. Examples of suitable materials include polyvinyl chloride (PVC), silicon polymers, polyamides (e.g. nylons), poly(ethylene terephthalate) (PET), poly-urethanes, polyether sulphones, and polycarbonates, including copolymers of such polymers, for instance a copolymer of a polyamide and a polyether (e.g. Pebax™).

A suitable supporting polymer (a) for use in the invention comprises functional moieties capable of undergoing polymerization reactions. When polymerized at the functional moieties, the supporting polymer is usually capable of forming a three-dimensional network, wherein another polymer may become entangled. The functional moiety of the polymer may be selected from the group consisting of radically reactive groups, such as amino, amido, sulphhydryl (SH), unsaturated esters, ethers and amides, alkyd/dry resins and alkene groups, in particular vinyl groups.

The average number of reactive moieties per molecule of supporting polymer (a) is preferably in the range of about 1.2 to about 64, more preferably in the range of about 1.2 to about 16, most preferably in the range of about 1.2 to about 8.

In one embodiment of the invention the supporting polymer comprises a backbone chosen from the group consisting of polyethers, polyesters, polyurethanes, polyepoxides, polyamides, polyacrylamides, poly(meth)acrylics, polyoxazolidones, polyvinyl alcohols, polyethylene imines, polypeptides and polysaccharides, such as cellulose or starch or any combination of the above, preferably polyether and/or polythioether. Preferably the supporting polymer further comprises double carbon-carbon bonds, which can be used to polymerize the polymer. Preferably the backbone moiety, preferably a polyether/polythioether moiety (moiety a1) is linked with at least two moieties (moiety a3) comprising a double carbon-carbon bond—in particular a moiety comprising a hydroxyl group and a radically reactive group as defined above, more in particular hydroxyacrylate or a hydroxymethacrylate which may comprise an alkyl side group. The link may be realized by any group. Preferably the link is realised by carbamate groups, i.e. —(NR)—(C=O)—O—, wherein R is hydrogen or an alkyl. Herein the carbamate may in particular originate from a polyisocyanate, in particular a di-isocyanate and an alcohol (e.g. from said hydroxyacrylate or hydroxymethacrylate and moiety a1). Other links that are envisaged, are in particular a thiocarbamate or a carbamide, ester, amide and an ether.

In particular preferred is a supporting polymer selected from the group consisting of polymers composed of at least a1) a polyether or polythioether; and/or a2) a moiety comprising at least two isocyanates; and/or a3) a hydroxyalkylacrylate, a hydroxyalkylmethacrylate, a polyhydroxyalkylacrylate and a polyhydroxymethacrylate Moiety a1) is preferably selected from polyalkylene glycols (such as polyethylene glycon (PEG) and polypropylene glycol (PPG) and combinations thereof) and polytetrahydrofuran. More preferably it is a copolymer of poly(-methyl-1,4-butanediol) and tetramethyleneglycol. Particularly preferred is poly(-methyl-1,4-butanediol) (tetramethyleneglycol) (PTGL). Such polymer is available from Hodogaya (as poly(2-methyl-1,4-butanediol)alt(tetramethyleneglycol).

In particular suitable examples of moiety a2) are 2,4-tolylene diisocyanate, 2,6-tolylene diisocyanate, 1,3-xylylene diisocyanate, 1,4-xylylene diisocyanate, 1,5-naphthalene diisocyanate, m-phenylene diisocyanate, p-phenylene diisocyanate, 3,3'-dimethyl-4,4'-diphenylmethane diisocyanate, 4,4'-diphenylmethane diisocyanate, 3,3'-dimethylphenylene diisocyanate, 4,4'-biphenylene diisocyanate, 1,6-hexane diisocyanate, isophorone diisocyanate, methylenebis(4-cyclohexylisocyanate), 2,2,4-trimethylhexamethylene diisocyanate, bis(2-isocyanatoethyl)fumarate, 6-isopropyl-1,3-phenyl diisocyanate, 4-diphenylpropane diisocyanate, hydrogenated diphenylmethane diisocyanate, hydrogenated xylylene diisocyanate, tetramethyl xylylene diisocyanate, lysine isocyanate, and the like. Moiety a2 is preferably selected from toluene diisocyanate and 4-cyclohexyldiisocyanate.

Moiety a3) is preferably selected from hydroxyalkylacrylate and hydroxyalkylmethacrylate. Herein the alkyl is preferably a C1-C18 alkyl. More preferably the alkyl is C2-C7, in view of the hydrophilic properties of the (meth)acrylate groups. Good results have been achieved with a compound wherein the alkyl is ethyl.

The supporting polymer (before curing) usually has a number average molecular weight (Mn) as determinable by size exclusion chromatography in tetrahydrofuran using polystyrene standards, of at least 300 g/mol, in particular at least 400 g/mol, more in particular at least 500 g/mol, preferably at least 750 g/mol more preferably at least 1000 g/mol. Usually the molecular weight is about 20000 g/mol or less, in particular 10000 g/mol or less, more in particular 5000 g/mol or less, preferably 3000 g/mol or less, in particular about 2500 g/mol or less.

The concentration of the supporting polymer in the primer layer is usually at least 65 wt %, based on the dry weight of the layer (i.e. without solvent). For improved adherence, the concentration is preferably at least 70 wt %, in particular at least 75 wt %, more in particular at least 80 wt %.

The upper limit is mainly determined by the desired concentration of one or more other components which may be present. In particular the concentration may be up to 100 wt %, more in particular up to 95 wt %, based on the total dry weight of the layer.

The primer layer may suitably be applied on the article in a manner known per se. Preferably a primer coating formulation according to the invention is used. Such formulation has been found to result in a coating with advantageous properties.

A primer coating formulation for providing an article with a primer layer according to the invention typically comprises
  (a) the supporting polymer (as identified above and/or in the claims), in a total concentration of 1-60 wt % in particular 1-20 wt %, based on the total weight of the formulation
  (b) an initiator, preferably a Norrish I type photo-initiator.

Typically said components, and optional one or more additives such as an antioxidant, an alicyclic compound, an aliphatic compound, an antioxidant and/or one or more additives known in the art to be suitable for use in a primer coating formulation, are dissolved in a suitable amount of solvent. In particular the solvent concentration may be at least 68 wt %, more in particular at least 75 wt %, preferably at least 80 wt %, more preferably at least 85 wt. %, even more preferably at least 90 wt % of a solvent. In view of handling properties (low viscosity) and/or in order to facilitate the application of the formulation such that a coating with the desired thickness is obtained, the total solids content is preferably 30 wt % or less, more preferably 20 wt % or less, even more preferably 15 wt % or less, in particular 10 wt % or less.

The solvent may be a single solvent or a mixture of solvents. It is chosen such that the polymers can be dissolved or at least dispersed therein. Preferably the primer coating formulation comprises an organic solvent having a boiling point below 140° C., in particular of 120° C. or less, more in particular of 100° C. or less. This may facilitate drying of the coating, if desired, especially if one or more further additives are present with a relatively low boiling point. Preferably the organic solvent is an alcohol, in particular a monohydric alcohol, more preferably methanol and/or ethanol. It has been found advantageous to include some water in the solvent, in particular in an amount that is soluble in the solvent, such as in a polar alcohol, in particular a C1-C4 monohydric alcohol. The water concentration may be at least 1 wt % based on the weight of the solvent in particular at least 2 wt %, more in particular at least 4 wt %, based on the total weight of the solvent. In view of dissolving/dispersing the supporting polymer, the water content is usually relatively low compared to the content of organic solvent, e.g. 10 wt % or less. It has been found that the presence of water facilitates dissolving the components into the solvent.

A preferred primer coating formulation of the invention comprises (a) at least 2 or at least 3 wt. % and/or up to 10 wt %, in particular up to 8 wt % of the supporting polymer, more preferably 2-8 wt %, in particular 3-8 wt. % of the supporting polymer. The concentration of the initiator (b) can be determined based upon the efficiency of the initiator, the desired curing rate and the amount of polymerizing components (typically component (a)). Usually, the total concentration of the initiator (b) is up to 10 wt %, based on the weight of component (a), in particular 0.5-8 wt % more in particular 1-6 wt %, preferably 2-6, more preferably 2-5 wt % based on the weight of component (a).

The coating formulation according to the invention can be cured in the presence of initiator (b). The term "to cure" includes any way of treating the formulation such that it forms a firm or solid coating. In particular "curing" is understood to refer to physical or chemical hardening or solidifying by any method, for example heating, cooling, drying, crystallization or curing as a result of a chemical reaction, such as radiation-curing or heat-curing. In the cured state all or part of the components in the coating formulation may be polymerized forming covalent linkages between all or part of the components, for example by using UV or electron beam radiation. However, in the cured state all or part of the components may also be ionically bonded, bonded by dipole-dipole type interactions, or bonded via Van der Waals forces or hydrogen bonds.

The coating formulation according to the invention can for example be cured using electromagnetic radiation, for example visible or UV light, electro-beam, plasma, gamma or IR radiation, in the presence of an initiator, for example a photo-initiator or thermal initiator, to form the medical coating. Examples of photo-initiators that can be used in the medical coating are free-radical photo-initiators, which are generally divided into two classes according to the process by which the initiating radicals are formed. Compounds that undergo unimolecular bond cleavage upon irradiation are termed Norrish Type I or homolytic photo-initiators. A Norrish Type II photo-initiator interacts with a second molecule, i.e. a synergist, which may be a low molecular weight compound of a polymer, in the excited state to generate radicals in a bimolecular reaction. In general, the two main reaction pathways for Norrish Type II photo-initiators are hydrogen abstraction by the excited initiator or photo-induced electron transfer. The mechanisms are further explained in WO06/056482.

Examples of suitable Norrish Type I or free-radical photo-initiators are benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, and the like. Commercial examples of suitable Norrish Type I photoinitiators are Irgacure 2959 (2-hydroxy-4'-(2-hydroxyethoxy)-2-methyl propiophenone), Irgacure 651 (benzildimethyl ketal or 2,2-dimethoxy-1,2-diphenylethanone, Ciba-Geigy), Irgacure 184 (1-hydroxy-cyclohexyl-phenyl ketone as the active component, Ciba-Geigy), Darocur 1173 (2-hydroxy-2-methyl-1-phenylpropan-1-one as the active component, Ciba-Geigy), Irgacure 907 (2-methyl-1-[4-(methylthio)phenyl]-2-morpholino propan-1-one, Ciba-Geigy), Irgacure 369 (2-benzyl-2-dimethylamino-1-(4-morpholinophenyl)-butan-1-one as the active component, Ciba-Geigy), Esacure KIP 150 (poly {2-hydroxy-2-methyl-1-[4-(1-methylvinyl)phenyl]propan-1-one}, Fratelli Lamberti), Esacure KIP 100 F (blend of poly {2-hydroxy-2-methyl-1-[4-(1-methylvinyl)phenyl]propan-1-one} and 2-hydroxy-2-methyl-1-phenyl-propan-1-one, Fratelli Lamberti), Esacure KTO 46 (blend of poly {2-hydroxy-2-methyl-1-[4-(1-methylvinyl)phenyl]propan-1-one}, 2,4,6-trimethylbenzoyldiphenyl-phosphine oxide and methylbenzophenone derivatives, Fratelli Lamberti), acylphosphine oxides such as Lucirin TPO (2,4,6-trimethylbenzoyl diphenyl phosphine oxide, BASF), Irgacure 819 (bis(2,4,6-trimethylbenzoyl)-phenyl-phosphine-oxide, Ciba-Geigy), Irgacure 1700 (25:75% blend of bis(2,6-dimethoxybenzoyl)2,4,4-trimethyl-pentyl phosphine oxide and 2-hydroxy-2-methyl-1-phenyl-propan-1-one, Ciba-Geigy), and the like. Also mixtures of type I photo-initiators can be used.

Examples of Norrish Type II photo-initiators that can be used in the medical coating formulation according to the invention include aromatic ketones such as benzophenone, xanthone, derivatives of benzophenone (e.g. chlorobenzophenone), blends of benzophenone and benzophenone derivatives (e.g. Photocure 81, a 50/50 blend of 4-methylbenzophenone and benzophenone), Michler's Ketone, Ethyl Michler's Ketone, thioxanthone and other xanthone derivatives like Quantacure ITX (isopropyl thioxanthone), benzil, anthraquinones (e.g. 2-ethyl anthraquinone), coumarin, or chemical derivatives or combinations of these photoinitiators.

Preferred is a photo-initiator that is water-soluble or can be adjusted to become water-soluble. Also preferred photo-initiators are polymeric or polymerisable photo-initiators.

In one embodiment of the invention the primer layer further comprises a hydrophilic polymer (c). It is contemplated that this helps to improve adherence of the functional layer to the primer layer, and thus to the article. The hydrophilic polymer (c), which may be present in the primer layer, can be chosen from the examples as defined below for hydrophilic polymer (C) which may be present in the functional layer. If a hydrophilic polymer is used in both the primer layer and the functional layer, said hydrophilic polymers may be the same or different.

If present, the concentration of the hydrophilic polymer in the primer layer may be at least 1 wt %, in particular at least 3 wt %, more in particular at least 5 wt % based on the total dry weight of the coating. Usually the concentration is up to 65 wt, preferably up to 50 wt %, more preferably up to 40 wt %, most preferably up to 30 wt %, in particular up to 20 wt %, more in particular up to 15 wt %, even more in particular up to 10 wt %. Suitably it may in particular be chosen in the range of 1 to 99 wt %, in particular 1-65 wt %, more in particular 1-40 wt %, preferably 1-30 wt %, more preferably 3-20 wt %, most preferably 5 to 10 wt %, based on the total dry weight of the coating.

The article may be provided with the primer coating formulation in any way to provide a layer, e.g. by dipping or spraying, of a suitable thickness.

For improved wear resistance and/or a relatively short curing time it is preferred that the primer coating formulation is applied in a relatively thin layer, in particular in an amount to provide a final layer thickness of 20 μm or less, more in particular of 7 μm or less, preferably of 5 μm or less, more preferably of 3 μm or less.

The thickness of the primer layer may be at least 0.1 μm, 0.2 μm, 0.3 μm, or 0.5 μm.

When the primer coating formulation has been applied to the surface it may be cured in any suitable way for the particular initiator and polymer combination.

The functional layer comprises multifunctional polymerizable compound (A), wherein $R_1$ particularly represents hydrogen, $CH_3$ or $CH_2OH$. Particularly suitable are multifunctional polymerizable compounds wherein $R_1$ and $R_2$ both represent hydrogen or wherein $R_1$ represents $CH_3$ and $R_2$ represents hydrogen.

Particularly suitable multifunctional polymerizable compounds (A) are polyether based (meth)acrylamides, for example polyethylene glycol diacrylamide and polyethylene glycol dimethacrylamide. Commercially available polyether multifunctional amines which can be used to produce multifunctional (meth)acrylamide polymerizable compounds include poly(ethylene glycol)bis(3-aminopropyl) terminated, Mw=1500 (Aldrich); PEG diamine (purely ethylene oxide units) P2AM-2 (molecular weight 2K), P2AM-3 (3.4K), P2AM-6 (6K), P2AM-8 (8K) and P2AM-10 (10K) (Sunbio), JEFFAMINE® D-230 polyetheramine, JEFFAMINE® D-400 polyetheramine, JEFFAMINE® D-2000, JEFFAMINE® D-4000, JEFFAMINE® XTJ-500 (ED-600), JEFFAMINE® XTJ D501 (ED-900), JEFFAMINE® XTJ-502 (ED-2003), JEFFAMINE®XTJ-590 diamine, JEFFAMINE® XTJ-542 diamine, JEFFAMINE® XTJ-548 diamine, JEFFAMINE® XTJ-559 diamine, JEFFAMINE® XTJ-556 diamine, JEFFAMINE® SD-231 (XTJ584), JEFFAMINE® SD401 (XTJ-585), JEFFAMINE® T-403 polyetheramine, JEFFAMINE® XTJ-509 polyoxypropylenetriamine, JEFFAMINE® T-5000 polyetheramine, and JEFFAMINE® ST-404 polyetheramine (XTJ-586).

Generally multifunctional polymerizable compound (A) has a number average molecular weight (Mn) of 500 g/mol or more, preferably 750 g/mol or more, more preferably 1000 g/mol or more. Generally multifunctional polymerizable compound (A) has a number average molecular weight (Mn) of 100,000 g/mol or less, preferably 10,000 g/mol or less, more preferably 6,000 g/mol or less, in particular 2,000 g/mol or less.

In addition to multifunctional polymerizable compound (A) as defined above, i.e. with n≥2, the composition may also comprise species according to formula (1) wherein n=1, i.e. molecules comprising only one reactive moiety. These monofunctional molecules may also be part of the network formed after curing. The average number of reactive moieties per molecule according to formula (1) is preferably in the range of about 1.2 to about 64, more preferably in the range of about 1.2 to about 16, most preferably in the range of about 1.2 to about 8.

The multifunctional polymerizable compound (A) may be used in the functional coating formulation in more than 0%, based on the total weight of the dry functional layer, i.e. without solvent, for example more than 5%, more than 10%, more than 20% or more than 30%. The multifunctional polymerizable compound can be present in the functional coating formulation up to 100%, however, more often the multifunctional polymerizable compound will be used up to 50, 60, 70, 80 or 90%, based on the total weight of the dry functional layer.

Hereinafter all percentages of components given in the application are based on the total weight of the dry layer.

In one embodiment of the invention a hydrophilic polymer (C) is present in the functional layer. Said hydrophilic polymer is capable of providing hydrophilicity to a coating and may be synthetic or bio-derived and can be a blend or a copolymer. As a hydrophilic polymer in principle any polymer may be used that is suitable to provide a lubricious hydrophilic coating. In particular suitable is such a polymer that is polymerizable, graftable and/or cross-linkable in the presence of an initiator.

A hydrophilic polymer is in particular a polymer that is water-soluble, capable to bind or hold a relatively large amount of water (for instance because it is water-gellable and/or water swellable). With respect to the capability to hold a large amount of water: the amount is in particular considered large if its water uptake capacity at 25° C. is at least about 25% of the weight of the polymer, more in particular at least about 50% of the weight of the polymer, more in particular at least about 100% of the weight of the polymer.

It has been found that adherence between the primer layer and the surface of the article and/or the primer layer and the functional layer is improved with increasing molecular weight of the hydrophilic polymer. Accordingly the weight average molecular weight of the hydrophilic polymer, as determinable by as determined by light scattering, optionally in combination with size exclusion chromatography, is usually at least 20 kg/mol, in particular at least 55 kg/mol, preferably at least 250 kg/mol, in particular at least 360 kg/mol, more preferably at least 500 kg/mol, in particular at least 750 kg/mol.

For practical reasons (ease of application and/or ease to realise uniform coating thickness) the weight average molecular weight (Mw) is usually up to 10 million, preferably up to 5 million g/mol, more preferably up to 3 million g/mol, most preferably up to 2 million g/mol, in particular up to 1.5 million g/mol, more in particular up to 1.3 million g/mol, even more in particular up to 1 million g/mol.

In particular polyvinylpyrollidone (PVP) and polyethyleneoxide (PEO) having an Mw of at least 100000 g/mol have been found to have a particular positive effect on lubricity and a low tendency to migrate out of the coating.

The hydrophilic polymer (C) may for instance be a prepolymer, i.e. a polymer comprising one or more polymerisable groups, in particular one or more radically polymerisable groups such as one or more vinyl groups.

However, also a polymer which is free of such polymerisable groups may be cured in the presence of an initiator, in particular by the formation of grafts when the formulation is exposed to light.

The hydrophilic polymer (C) may be non-ionic or ionic or a mixture of non-ionic and ionic polymers.

Non-ionic polymers include but are not limited to poly (lactams), for example polyvinylpyrrolidone (PVP), polyurethanes, homo- and copolymers of acrylic and methacrylic acid, polyvinyl alcohol, polyvinylethers, maleic anhydride based copolymers, polyesters, vinylamines, polyethylene imines, polyethylene oxides, poly(carboxylic acids), polyamides, polyanhydrides, polyphosphazenes, cellulosics, for example methyl cellulose, carboxymethyl cellulose, hydroxymethyl cellulose, and hydroxypropyl cellulose, heparin, dextran, polypeptides, for example collagens, fibrins, and elastin, polysaccharides, for example chitosan, hyaluronic acid, alginates, gelatin, and chitin, polyesters, for example polylactides, polyglycolides, and polycaprolactones, polypeptides, for example collagen, albumin, oligo peptides, polypeptides, short chain peptides, proteins, and oligonucleotides.

In particular for polyvinylpyrrolidone (PVP) and polymers of the same class, a polymer having a molecular weight corresponding to at least K15, more in particular K30, even more in particular K80 is preferred. Particular good results have been achieved with a polymer having a molecular weight corresponding to at least K90. Regarding the upper limit, a K120 or less, in particular a K100 is preferred. The K-value is the value as determinable by the Method W1307, Revision May 2001 of the Viscotek Y501 automated relative viscometer. This manual may be found at www.ispcorp.com/products/hairscin/index_3.html.

If an ionic polymer is used it may be a polyelectrolyte. Herein a polyelectrolytes is defined as a high molecular weight linear, branched or cross-linked polymer composed of macromolecules comprising constitutional units, in which between 5 and 100% of the constitutional units are in the ionized form in the hydrophilic coating. Herein a constitutional unit is understood to be for example a repeating unit, for example a monomer. A polyelectrolyte herein may refer to one type of polyelectrolyte composed of one type of macromolecules, but it may also refer to two or more different types of polyelectrolytes composed of different types of macromolecules. Preferably the polyelectrolytes have a number average molecular weight (Mn) of between 1,000 to 1,000,000 g/mol.

Suitable polyelectrolytes are for example salts of homo- and co-polymers of acrylic acid, methacrylic acid, maleic acid, fumaric acid, and sulfonic acid, and quaternary ammonium salts and mixtures and/or derivatives thereof. Examples of suitable polyelectrolytes are polyacrylamide-co-acrylic acid sodium salt, polyacrylic acid sodium salt, polymethacrylic acid sodium salt, polyacrylamido-2-methyl-1-propanesulfonic acid sodium salt, poly(4-styrene sulfonic acid) sodium salt, poly(acrylamide-co-dialkyl ammonium chloride), quaternized poly[bis-(2-chloroethylether-alt-1,3-bis[3-(dimethylamino)propyl]urea], polyallylammonium phosphate, poly(diallyldimethylammonium chloride), poly (sodium trimethyleneoxyethylene sulfonate), poly(dimethyldodecyl(2-acrylamidoethyl) ammonium bromide), poly(2-N methylpyridiniumethylene iodine), polyvinylsulfonic acids, and salts of poly(vinyl)pyridines, polyethyleneimines, and polylysines.

If present, the non-ionic or ionic hydrophilic polymer may be used in more than 0 wt % of the coating formulation, for example more than 1 wt %, more than 2 wt %, or more than 10 weight %, based on the total weight of the dry hydrophilic coating. The hydrophilic polymer can be present in the coating formulation up to 90 wt %, however, more often the hydrophilic polymer will be used up to 50, 60, 70 or 80 wt %, based on the total weight of the dry hydrophilic coating.

If an hydrophilic polymer (C) is present, the ratio multifunctional polymerizable compound (A):hydrophilic polymer (C) may be chosen within wide limits, depending upon the intended result. In particular the weight to weight ratio of the hydrophilic polymer to multifunctional polymerizable compound is chosen between 20:1 and 1:20, in particular between 15:1 and 1:15, more in particular between 12:1 and 1:12.

The invention also relates to a coating formulation for preparing a functional layer. Herein a coating formulation usually refers to a liquid coating formulation, e.g. a solution or a dispersion comprising a liquid medium. Herein any liquid medium that allows application of the coating formulation on a surface would suffice. The coating formulation thus further comprises a liquid medium in a sufficient amount to disperse or dissolve the other components of the formulation. The concentration of the liquid medium is usually at least 68 wt. %, preferably at least 75 wt. %, more preferably at least 80 wt. %, even more preferably at least 85 wt. % of the total weight of the liquid coating formulation. In view of handling properties (low viscosity) and/or in order to facilitate the application of the formulation such that a coating with the desired thickness is obtained, the amount of liquid medium in the formulation is preferably relatively high. For that reason the total solids content is preferably 20 wt. % or less.

The liquid medium may be a single liquid medium or a mixture. It is chosen such that the polymers can be dissolved or at least dispersed therein. In particular for dissolving or dispersing the hydrophilic polymer well, it is preferred that the liquid medium is a polar liquid. In particular, a liquid is considered polar if it is soluble in water. Preferably it comprises water and/or an organic solvent soluble in water, for example an alcohol, acetone, methylethyl ketone, tetrahydrofuran, dichloromethane, and aqueous mixtures or emulsions, preferably an alcohol, more preferably a C1-C4 alcohol, in particular methanol and/or ethanol. In case of a mixture, the ratio water to organic solvent, in particular one or more alcohols, may be in the range of about 25:75 to 75:25, in particular 40:60 to 60:40, more in particular 45:55 to 55:45.

The functional coating formulation can be subjected to curing, as described above for the primer coating formulation, in particular in the presence of an initiator (B), for example a photo-initiator or thermal initiator, to form the hydrophilic coating. Both Norrish Type I and Norrish Type II photo-initiators may be applied. Examples of Norrish Type I photo-initiators, which are described above for the primer coating formulation, can also be applied in the functional coating formulation. Examples of Norrish Type II photo-initiators are benzophenone hydroxymethylphenylpropanone, dimethoxyphenylacetophenone, 2-methyl-I-4-(methylthio)-phenyl-2-morpholino-propanone-1,1-(4-isopropylphenyl)-2-hydroxy-2-methylpropan-1-one, 1-(4-dodecyl-phenyl)-2-hydroxy-2-methylpropan-1-one, diethoxyphenyl acetophenone, and the like. Phosphine oxide photoinitator types (e.g., Lucirin TPO by BASF) such as benzoyl diaryl phosphine oxide photo-initiators may be used.

The invention also relates to a functional coating formulation comprising
(A) a multifunctional polymerizable compound according to formula (1) in a total concentration of 0.5-60 wt. %, in particular 0.5-30 wt %, preferably 0.5-20 wt %, more preferably 0.5-10 wt %, even more preferably 1-5 wt %, based on the total weight of the formulation;
(B) a photo-initiator, preferably in a total concentration of 0.1-10 wt. based on the total weight of a) and b);
(C) optionally a functional polymer in a total concentration of 0-60 wt %, based on the total weight of the formulation, in particular 0.5-30 wt %, preferably 0.5-20 wt %, more preferably 0.5-10 wt %, even more preferably 1-5 wt %;

And at least 68 wt %, preferably at least 75 wt %, more preferably at least 80 wt %, even more preferably at least 85 wt % of a solvent, wherein the components A), B), and optionally (C) are dissolved or dispersed.

The functional coating formulation may further comprise a surfactant (D), preferably in a concentration of 0.1-10 wt. based on the total weight of (A) and (C).

The invention also relates to a coating system for providing an article with a primer layer and a functional layer, comprising a primer coating formulation and a functional coating formulation according to the invention.

In an embodiment of the invention the functional coating formulation according to the invention further comprises at least one surfactant (D), which can improve the surface properties of the coating. Surfactants constitute the most important group of detergent components. Generally, these are water-soluble surface-active agents comprised of a hydrophobic portion, usually a long alkyl chain, attached to hydrophilic or water solubility enhancing functional groups. Surfactants can be categorized according to the charge present in the hydrophilic portion of the molecule (after dissociation in aqueous solution): ionic surfactants, for example anionic or cationic surfactants, and non-ionic surfactants. Examples of ionic surfactants include Sodium dodecylsulfate (SDS), Sodium cholate, Bis(2-ethylhexyl)sulfosuccinate Sodium salt, Cetyltrimethylammoniumbromide (CTAB), Lauryldimethylamine-oxide (LDAO), N-Laurylsarcosine Sodium salt and Sodium deoxycholate (DOC). Examples of non-ionic surfactants include Alkyl Polyglucosides such as TRITON™ BG-10 Surfactant and TRITON CG-110 Surfactant, Branched Secondary Alcohol Ethoxylates such as TERGITOL™ TMN Series, Ethylene Oxide/Propylene Oxide Copolymers, such as TERGITOL L Series, and TERGITOL XD, XH, and XJ Surfactants, Nonylphenol Ethoxylates such as TERGITOL NP Series, Octylphenol Ethoxylates, such as TRITON X Series, Secondary Alcohol Ethoxylates, such as TERGITOL 15-S Series and Specialty Alkoxylates, such as TRITON CA Surfactant, TRITON N-57 Surfactant, TRITON X-207 Surfactant, Tween 80 and Tween 20.

Typically 0.001 to 1 wt % of surfactant (D) is applied, preferably 0.05-0.5 wt %, based on the total weight of the dry functional layer.

One or more other additives which may be present in the functional coating formulation according to the invention are for example amine compounds, for example diallylamine, diisopropylamine, diethylamine, and diethylhexylamine; antioxidants; water-soluble radical stabilizers; UV absorbers; light stabilizers; (silane) coupling agents; coating surface improvers; heat polymerization inhibitors; leveling agents; surfactants; colorants, for example a pigment or a dye; discolorants; preservatives; dispersing agents; plasticizers; lubricants; solvents; fillers; wettability improvers; urea; and chain transfer agents. The colorant can be a pigment or dye.

The coating according to the invention can be coated on an article. The coating can be coated on a substrate which may be selected from a range of geometries and materials. The substrate may have a texture, such as porous, non-porous, smooth, rough, even or uneven. The substrate supports the coating on its surface. The coating can be on all areas of the substrate or on selected areas. The coating can be applied to a variety of physical forms, including films, sheets, rods, tubes, molded parts (regular or irregular shape), fibers, fabrics, and particulates. Suitable surfaces for use in the invention are surfaces that provide the desired properties such as porosity, hydrophobicity, hydrophilicity, colorisability, strength, flexibility, permeability, elongation abrasion resistance and tear resistance. Examples of suitable surfaces are for instance surfaces that consist of or comprise metals, plastics, ceramics, glass and/or composites. The coating may be applied directly to the said surfaces or may be applied to a pretreated or coated surface where the pretreatment or coating is designed to aid adhesion of the coating to the substrate.

In one embodiment of the invention the coating according to the invention is coated on a biomedical substrate. A biomedical substrate refers, in part, to the fields of medicine, and the study of living cells and systems. These fields include diagnostic, therapeutic, and experimental human medicine, veterinary medicine, and agriculture. Examples of medical fields include opthalmology, orthopedics, and prosthetics, immunology, dermatology, pharmacology, and surgery; non-limiting examples of research fields include cell biology, microbiology, and chemistry. The term "biomedical" also relates to chemicals and compositions of chemicals, regardless of their source, that (i) mediate a biological response in vivo, (ii) are active in an in vitro assay or other model, e.g., an immunological or pharmacological assay, or (iii) can be found within a cell or organism. The term "biomedical" also refers to the separation sciences, such as those involving processes of chromatography, osmosis, reverse osmosis, and filtration. Examples of biomedical articles include research tools, industrial, and consumer applications. Biomedical articles include separation articles, implantable articles, and ophthalmic articles. Ophthalmic articles include soft and hard contact lenses, intraocular lenses, and forceps, retractors, or other surgical tools that contact the eye or surrounding tissue. A preferred biomedical article is a soft contact lens made of a silicon-containing hydrogel polymer that is highly permeable to oxygen. Separation articles include filters, osmosis and reverse osmosis membranes, and dialysis membranes, as well as bio-surfaces such as artificial skins or other membranes. Implantable articles include catheters, and segments of artificial bone, joints, or cartilage. An article may be in more than one category, for example, an artificial skin is a porous, biomedical article. Examples of cell culture articles are glass beakers, plastic petri dishes, and other implements used in tissue cell culture or cell culture processes. A preferred example of a cell culture article is a bioreactor micro-carrier, a silicone polymer matrix used in immobilized cell bioreactors, where the geometry, porosity, and density of the particulate micro-carrier may be controlled to optimize performance. Ideally, the micro-carrier is resistant to chemical or biological degradation, to high impact stress, to mechanical stress (stirring), and to repeated steam or chemical sterilization. In addition to silicone polymers, other materials may also be suitable. This invention may also be applied in the food industry, the paper printing industry, hospital supplies, diapers and other liners, and other areas where hydrophilic, wettable, or wicking articles are desired.

The invention also relates to a medical, optionally hydrophilic coating obtainable by applying the coating formulation according to the invention to a substrate and curing it. The invention further relates to a lubricious coating obtainable by wetting said hydrophilic coating, and to the use of a multifunctional polymerizable compound according to formula (1) in a hydrophilic coating that also comprises a an ionic compound.

The medical device can be an implantable device or an extracorporeal device. The devices can be of short-term temporary use or of long-term permanent implantation. In certain embodiments, suitable devices are those that are typically used to provide for medical therapy and/or diagnostics in heart rhythm disorders, heart failure, valve disease, vascular disease, diabetes, neurological diseases and disorders, orthopedics, neurosurgery, oncology, opthalmology, and ENT surgery.

Suitable examples of medical devices include, but are not limited to, a stent, stent graft, anastomotic connector, synthetic patch, lead, electrode, needle, guide wire, catheter, sensor, surgical instrument, angioplasty balloon, wound drain, shunt, tubing, infusion sleeve, urethral insert, pellet, implant, blood oxygenator, pump, vascular graft, vascular access port, heart valve, annuloplasty ring, suture, surgical clip, surgical staple, pacemaker, implantable defibrillator, neurostimulator, orthopedic device, cerebrospinal fluid shunt, implantable drug pump, spinal cage, artificial disc, replacement device for nucleus pulpous, ear tube, intraocular lens and any tubing used in minimally invasive surgery.

Articles that are particularly suited to be used in the present invention include medical devices or components such as catheters, guidewires, stents, syringes, metal and plastic implants, contact lenses, medical tubing, and extracorporeal devices.

The coating formulation can be applied to the substrate by for example dip-coating. Other methods of application include spray, wash, vapor deposition, brush, roller, curtain, spin coating and other methods known in the art.

The thickness of the functional layer may be controlled by altering soaking time, drawing speed, viscosity of the coating formulation and the number of coating steps. Typically the thickness of the functionally layer ranges from 0.05-300 µm, preferably 0.1-200 µm.

In an embodiment, the surface of the article is subjected to oxidative, photo-oxidative and/or polarizing surface treatment, for example plasma and/or corona treatment in order to improve the adherence of the coating which is to be provided. Suitable conditions are known in the art.

Application of the formulation of the invention may be done in any manner. Curing conditions can be determined, based on known curing conditions for the photo-initiator and polymer or routinely be determined.

In general, curing may be carried out at any suitable temperature depending on the substrate, as long as the mechanical properties or another property of the article are not adversely affected to an unacceptable extent.

Intensity and wavelength of the electromagnetic radiation can routinely be chosen based on the photo-initiator of choice. In particular, a suitable wavelength in the UV, visible or IR part of the spectrum may be used.

The invention will be further illustrated by the following examples.

EXAMPLES

1. Synthesis of Multifunctional Polymerizable Compounds 1.1 Synthesis of PEG-diacrylate; PEGDA

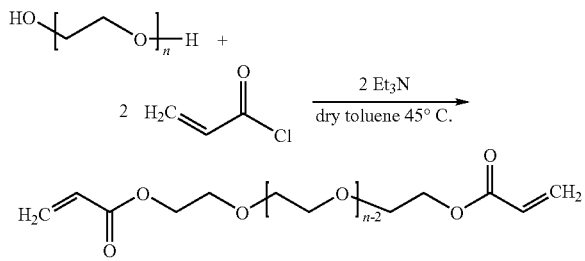

PEG$_{4000}$DA

PEG (150 g, 75 mmol OH, Biochemika Ultra from Fluka [95904], #427345/1, OH-value: 28.02 mg KOH/g, 499.5 meq/kg, Mn: 4004 mol/g) was dissolved at 45° C. in 350 mL of dry toluene (Merck, pro analysis, dried on molsieves (4 Å)) under nitrogen atmosphere, Irgacure 1035 (0.2 g~0.15 w %, Ciba Specially Chemical) was added as a radical stabilizer. The PEG/toluene solution was distilled azeotropically overnight (50° C./70 mbar) leading the condensing toluene over 4 Å mol sieves. It is important to determine accurately the hydroxyl value for each batch of PEG by OH titration (see analysis) to calculate the amount of acryloyl chloride (Merck, for synthesis, stored at 5° C. and used as received) to be added and to determine the conversion during the reaction.

Triethylamine (9.10 grams, 90 mmol, Aldrich, 99.5%, kept under nitrogen atmosphere and is used as received) was added to the reaction mixture, followed by the drop wise addition over 1 h of acryloyl chloride (8.15 grams, 90 mmol, (Merck, for synthesis, is stored at 5° C. and used as received) dissolved in 50 mL of dry toluene. The Acryloyl chloride and triethyl amine used should be colorless liquids. The reaction mixture was stirred for 2 to 4 hours at 45° C. under nitrogen atmosphere. During the reaction the temperature was kept at 45° C. to prevent crystallization of PEG.

To check the conversion a sample was withdrawn from the reaction mixture, dried and dissolved in deuterated chloroform, trifluoro acetic anhydride (TFAA) was added and a $^1$H-NMR spectrum was recorded. TFAA reacts with any remaining hydroxyl groups to form a trifluoro acetic ester, which can be easily detected using $^1$H-NMR spectroscopy (see analysis). When the conversion was <98% (±0.5%) an additional 10 mmol of acryloyl chloride and triethylamine were added to the reaction mixture allowing it to react for one additional hour.

At a conversion >98% (±0.5%) the warm solution was quickly filtrated to remove triethyl amine HCl salts. Approximately 300 mL of toluene was removed under vacuum (50° C., 20 mbar). The remaining solution was kept at 45° C. in a heated dropping funnel and added drop wise to a 1 L of diethyl ether (cooled on an ice bath, Merck). The ether suspension was cooled for 1 additional hour before the PEG diacrylate product was obtained by filtration. The product was dried overnight at room temperature under reduced air atmosphere (300 mbar). Yield: 80-90% as white crystals.

NMR: 300 MHz $^1$H-NMR spectrum of PEG$_{4000}$DA in CDCl$_3$ (TMS). 6.40 (doublet, 2H), 6.15 (multiplet, 2H), 5.8 (doublet, 2H), CH$_2$=CH— and CH$_2$=CH—; 4.3 (triplet, 4H), —(C=O)OCH$_2$—; 3.75 (triplet, 4H), —(C=O)OCH$_2$CH$_2$—; 3.65 (multiplet, 370H), —OCH$_2$CH$_2$O—.

The NMR pattern confirmed the formation of PEG$_{4000}$DA.

The IR pattern confirmed the formation of PEG$_{4000}$DA

The synthesis and characterization of PEG$_{2000}$DA was similar to synthesis and characterization of PEG$_{4000}$DA. Instead of PEG$_{4000}$ (M$_r$ 3500-4500; Biochemika Ultra from Fluka), PEG$_{2000}$ (M$_r$ 1900-2200; Biochemika Ultra from Fluka) was used.

1.2 Synthesis of PEG-diacrylamide; PEG(AM)$_2$

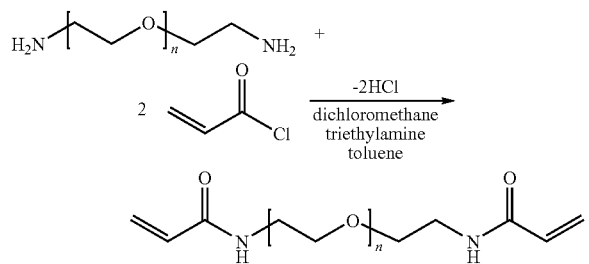

20 g (13.3 mmol) of PEG-diamine (M$_n$ 1500 g/mol; Aldrich) was azeotropically distilled in 400 mL of toluene under nitrogen, removing about 100 mL of toluene. The solution was cooled at room temperature under nitrogen and then cooled in an ice bath. 50 mL of dichloromethane (Merck) were added. 4.04 g (39.7 mmol) of triethylamine was added dropwise followed by the dropwise addition of 3.48 g (39.7 mmol) of acryloyl chloride (used without further purification). The reaction proceeded overnight under nitrogen. The solution was cooled in an ice bath to precipitate NEt$_3$.HCl salts and was then filtrated. After adding 1% (w/w) Irganox 1035, the filtrate was concentrated under vacuum. The concentrate was redissolved in 75 mL of dichloromethane, followed by precipitation in 1.5 L ice cold diethyl ether. The product was collected by filtration and subsequent washing with diethyl ether.

$^1$H-NMR (CDCl$_3$, 22° C.) δ (TMS)=6.7 ppm (2H, —NH—); 6.2 & 6.1 ppm (4H, CH$_2$=CH—); 5.6 ppm (2H, CH$_2$=CH—); 3.6 ppm (164H, —O—CH$_2$—CH$_2$— and —O—CH$_2$—CH$_2$—CH$_2$—); 1.8 ppm (4H, —O—CH$_2$—CH$_2$—CH$_2$—).

The NMR spectrum confirmed the formation of PEG(AM)$_2$. From the integration of the NMR peaks at 6.2 and 6.1 ppm, respectively 1.8 ppm, about 99% of the PEG-diamine was estimated to be converted into PEG(AM)$_2$.

The IR spectrum confirmed the formation of PEG(AM)$_2$.

1.3 Synthesis of PEG-dimethacrylamide; PEG(MAM)$_2$

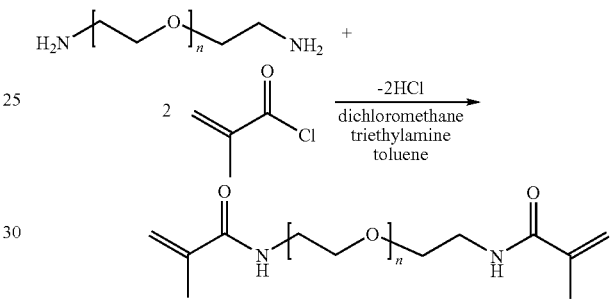

Synthesis: similar to synthesis of PEG-diacrylamide.

Instead of acryloyl chloride, methacryloyl chloride (Acros) was used.

$^1$H-NMR (CDCl$_3$, 22° C.) δ (TMS)=6.8 ppm (2H, —NH—); 5.7 & 5.3 ppm (4H, CH$_2$=C); 3.6 ppm (164H, —O—CH$_2$—CH$_2$— and —O—CH$_2$—CH$_2$—CH$_2$—); 1.95 ppm (CH$_3$ methacrylamide); 1.8 ppm (4H, —O—CH$_2$—CH$_2$—CH$_2$—).

The NMR pattern confirmed the formation of PEG(MAM)$_2$. From the integration of the NMR peaks at 5.7 and 5.3 ppm, respectively 1.8 ppm, about 90% of the PEG-diamine was estimated to be converted into PEG(MAM)$_2$.

The IR pattern confirmed the formation of PEG(MAM)$_2$.

1.4 Synthesis of PTGL1000(T-H)$_2$

In a dry inert atmosphere toluene diisocyanate (TDI or T, Aldrich, 95% purity, 87.1 g, 0.5 mol), Irganox 1035 (Ciba Specialty Chemicals, 0.58 g, 1 wt % relative to hydroxy ethyl acrylate (HEA or H)) and tin(II) 2-ethyl hexanoate (Sigma, 95% purity, 0.2 g, 0.5 mol) were placed in a 1 liter flask and stirred for 30 minutes. The reaction mixture was cooled to 0° C. using an ice bath. HEA (Aldrich, 96% purity, 58.1 g, 0.5 mol) was added dropwise in 30 min, after which the ice bath was removed and the mixture was allowed to warm up to room temperature. After 3 h the reaction was complete. Poly (2-methyl-1,4-butanediol)-alt-poly(tetramethyleneglycol) (PTGL, Hodogaya, M$_n$=1000 g/mol, 250 g, 0.25 mol) was added dropwise in 30 min. Subsequently the reaction mixture was heated to 60° C. and stirred for 18 h, upon which the reaction was complete as indicated by GPC (showing complete consumption of HEA), IR (displayed no NCO related bands) and NCO titration (NCO content below 0.02 wt %).

2. Formulations

TABLE 1

Primer formulation Example 1 and Comparative Experiment A:

| Compound | Amount (%, w/w) |
|---|---|
| $PTGL_{1000}(TDI-HEA)_2$ | 20 |
| Ethanol (Merck, 96%, extra pure PH EUR, BP) | 79.6 |
| Irgacure 2959 (Aldrich) | 0.4 |

TABLE 2

Primer coating formulation (Examples 2 and 3 and Comparative Experiment B):

| Compound | Amount (g) | Amount (%, w/w) |
|---|---|---|
| $PTGL_{1000}(TDI-HEA)_2$ | 29.82 | 5.04 |
| PVP 1.3 M (Povidone, Sigma-Aldrich) | 5.25 | 0.89 |
| Ethanol | 555.52 | 93.84 |
| Irgacure 2959 | 1.40 | 0.23 |

TABLE 3

Coating formulation Example 1 and Comparative Experiment A:

| Compound | Amount (%, w/w) |
|---|---|
| Multifunctional polymerizable compound: $PEG(AM)_2$ (Example 1) PEGDA (Comp. Exp. A) | 20 |
| Ethanol | 79.6 |
| Irgacure 2959 (Aldrich) | 0.4 |

TABLE 4

Functional coating formulation (Examples 2 and 3 and Comparative Experiment B):

| Compound | Amount (g) | Amount (%, w/w) |
|---|---|---|
| Multifunctional polymerizable compound: PEGDA/PEG(AM)$_2$/PEG(MAM)$_2$ | 10 | 4.71 [4.71] |
| PVP 1.3 M | 6.66 | 3.14 [3.14] |
| Poly(acrylamide-co-acrylic acid)•Na$^+$ 20% (w/w) acrylamide/14.5% (w/w) Na$^+$ (Aldrich) | 3.34 | 1.58 [1.57] |
| Methanol | 95.92 | 45.24 [45.20] |
| Water | 95.92 | 45.24 [45.20] |
| Irgacure 2959 | 0.2 | 0.09 [0.09] |
| [Tween 80] | [0.2] | [0.09] |

For the primer formulation as well as for the coating formulation the compounds were dissolved in the solvent under stirring at room temperature. To obtain the coating formulation, a formulation containing all of the compounds indicated above except the multifunctional polymerizable compound was prepared the day before the start of the experiment. The experiment was started with the dissolution of the multifunctional polymerizable compound in this formulation (within one hour the multifunctional polymerizable compound was dissolved).

3. Methods

3.1. NMR Measurements

Nuclear magnetic resonance (NMR) measurements were performed on a Varian Inova 300 spectrometer.

NMR experiments were performed at 22° C. for the synthesized multifunctional polymerizable compounds dissolved in deuterated chloroform.

3.2. FTIR Measurements

Fourier transformed infrared (FTIR) measurements were performed by means of a Perkin Elmer Spectrum One spectrophotometer using the Spectrum software.

The synthesized multifunctional polymerizable compounds were analysed in the form of potassium bromide (Uvasol; Merck) pills.

3.3. Coating on PET Film

Example 1 and Comparative Experiment A

The primer coating formulation according to Table 1 was coated on 120 μm PET foil using Meyenbar #12 resulting in a dry film thickness of approximately 550 nm. The primer coating formulation was cured with 1.10 J/cm$^2$ using a D-lamp in air. Subsequently the coating formulations of Table 3 were coated on the primer. The coatings were left for 1 min to dry at 25° C. and were exposed to a single UV pass with 1.10 J/cm$^2$ using a D-lamp in air. The resulting coating thickness was 2 μm.

3.4. Dipcoating

Examples 3 and 4 and Comparative Experiment C

Dipcoating was performed with a Harland PCX coater. The intensity of the lamps was measured by means of a Harland UVR 335 (also known as IL 1400) equipped with an International Light detector SED 005#989. Input optic: W#11521, filter wbs320#27794.

Commercially available medical grade PVC tubing (14 French; Raumedic) was used. The tubing was sealed at the bottom end in order to prevent the coating formulation to reach the inside of the tubing during dipping. A guidewire was inserted in the tubing to fix the tubing and to attach it in the holder of the coater. The tubing was cleaned with lens tissues (Whatman) immersed in a 96% (w/v) aqueous ethanol solution (Merck). The assembly was subsequently dipped in the primer and the topcoat formulations using the coater. The intensity of the lamps was on average 60 mW/cm$^2$. To measure the intensity of the lamps, the instruction manual of International Light was applied, which is available on the internet: www.intl-light.com. The tubing was dipped in the primer formulation for 10 seconds, moved up with a speed of 0.3 cm/s and cured for 15 seconds with a total dose of 0.9 J/cm$^2$. The tubing was then dipped in the topcoat formulation for 10 seconds, moved up with a speed of 1.5 cm/s and cured for 360 seconds with a total dose of 21.6 J/cm$^2$. After drying for a night at room temperature, the lubricity, wear resistance and dry-out time of the coatings were determined.

3.5. Determination of Lubricity and Wear Resistance of Coatings

Examples 3 and 4 and Comparative Experiment C

A Harland FTS 5000 friction tester was used. Friction tester pads were used from Harland Medical Systems, P/N 102692, FTS 5000 Friction Tester Pads, 0.125*0.5*0.125, 60 durometer.

A guide wire was inserted in the tubing to fix the tubing and to attach it in the holder of the friction tester. If the test was to be run wet, the clamp was positioned over the container such that the clamp pads were submerged. The holder was moved down such that the (coated) tubing was also immersed in the water. After immersing for one minute the clamp was closed and fixed the tubing with a clamp force of 300 g. The holder moved up for 10 cm and the friction force was measured during the moving-up. The following parameters were applied: 25 testing cycles, pulling speed 1.0 cm/s, acceleration time 2.0 s. When compounds were leaching out of the coating, the clamp pads of the friction tester were cleaned before each testing cycle.

The dry-out time can be determined by measuring the lubricity (as friction in g) as a function of time. In the test to measure the dry-out time 5 testing cycles were applied with a time interval of 300 s. All other parameters are the same as in the lubricity test.

3.6. Stability Tests

Example 1 and Comparative Experiment A

Effect of Multifunctional Polymerizable Compound on Rub Resistance

In order to test the stability of the coating formulations of Example 1 and Comparative Example A the following test was performed.

The films prepared according to 3.3. were incubated in standard phosphate buffer solutions ("PBS buffers") for 110 hours at 45° C. The rub resistance was immediately checked after annealing using a single index finger tip using 5 drops of water. The results are shown in Table 6.

3.7. Stability Tests

Example 2 and Comparative Experiment B

Effect of Multifunctional Polymerizable Compound on the Lubricity of the Lubricious Coating Upon Incubating the Coating Formulation In order to test the stability of the coating formulations used to prepare the lubricious coating the following test was performed Coating formulations according to Table 5, comprising respectively PEGDA and PEG(AM)$_2$, were incubated at 50° C. in a closed container for 0 and 2 days (PEGDA) and 0, 2 and 7 days (PEG(AM)$_2$). Tubings were coated with the resulting coating formulations according to the method described in 3.4.

The tubings coated with the coating formulation comprising PEGDA were tested twice in a series (catheter still immersed in water). After the 25 cycles of the first test the coated tubing was kept in the water for 10 minutes before starting the second test consisting of 25 cycles. The results are given in FIG. 1.

The tubings coated with the coating formulation comprising PEG(AM)$_2$ were tested only once. The results are given in FIG. 2.

4. Results

4.1. Example 1 and Comparative Experiment A

Stability of the Coating Determined by Rub Tests

TABLE 5

Example 1 and Comparative Experiment A: stability of coatings comprising PEG(AM)$_2$ and PEGDA, respectively.

| | Primer | Multifunctional polymerizable compound | Rubbing performance |
|---|---|---|---|
| Example 1 | Table 1 | PEG(AM)$_2$ | − |
| Comparative Experiment A | Table 1 | PEGDA | + |

Table 5 shows that the coating according to Example 1, prepared form a coating formulation containing PEG(AM)$_2$, Irgacure 2959 and ethanol is much more stable against rubbing than an equivalent coating containing PEGDA instead of PEG(AM)$_2$

4.2. Examples 2 and 3 and Comparative Experiment B 4.2 1. Appearance of Coatings Curing fresh formulations containing PEG(AM)$_2$ (Example 2), PEG(MAM)$_2$ (Example 3) and PEGDA (Comparative Experiment B) resulted in clear coatings. Upon incubating the coating formulations containing PEGDA at 50° C. in a closed container, the resulting coatings became more and more opaque. The coating made from the formulation containing PEG(AM)$_2$ and PEG(MAM)$_2$ remained clear upon incubating the formulation at 50° C. This shows the improved stability of the coating formulation.

4.3.2. Lubricity and Wear Resistance

FIG. 1 (Comparative Experiment B) shows that the lubricity, expressed as the friction force (the higher the friction force, the lower the lubricity), is significantly reduced after incubating the coating formulations comprising PEGDA used for preparing the lubricious coatings for 2 days at 50° C. (closed triangles): friction forces in the range 40-80 g were measured. In fact, for the coatings prepared from a PEGDA containing coating formulation parts of the coating were removed by the clamp pads of the friction tester during the first cycles of the first test series. As a result, the coatings were damaged. The second test of the test series after 2 days of incubation therefore resulted in even higher friction forces (open triangles) in the range 70-140 g. This was not observed for the coatings prepared from the fresh coating formulation (0 days incubation) (closed and open squares): friction forces of approximately 10 g were measured in both test series.

FIG. 2 (Example 2) shows much more favorable results for the lubricious coatings prepared from the formulation containing PEG(AM)$_2$. Even the coatings prepared from coating formulations incubated at 2 or 7 days still feature a high lubricity (low friction force): in all measurements the friction force was below 10 g. All coatings stayed intact during the friction test. The incubation of the formulation had no influence on the wear resistance of the resulting coating.

The invention claimed is:

1. A medical device comprising a cured coating, wherein the cured coating comprises at least two layers comprising an inner layer and an outer layer, wherein the inner layer is a primer layer comprising a supporting network and formed by curing a primer layer formulation comprising a supporting polymer, and wherein the outer layer is a functional layer formed by curing a functional layer formulation, the functional layer formulation comprising:

(A) at least one multifunctional polymerizable compound according to formula (1):

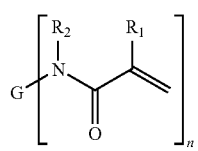

wherein

G is a polymer and is a residue of a hydrophilic polyfunctional compound having at least n functional groups;

each $R_1$ and each $R_2$ independently represents hydrogen or a group selected from substituted and unsubstituted hydrocarbons which optionally contain one or more heteroatoms; and n is an integer having a value of 2-100.

2. The medical device according to claim 1, wherein the multifunctional polymerizable compound (A) has a number average molecular weight (Mn) of between 500 and 2000 g/mol.

3. The medical device according to claim 1, wherein the functional layer formulation further comprises a functional polymer (C).

4. The medical device according to claim 3, wherein
the concentration of the supporting polymer in the primer layer formulation is in the range of 50 to 100 wt %, based on the total dry weight of the of the primer layer formulation;
the concentration of the multifunctional polymerizable compound (A) in the functional layer formulation is in the range of 8-60% based on the total dry weight of the functional layer formulation; and
the concentration of the functional polymer (C) in the functional layer formulation is in the range of 40 to 95 wt %, based on the total dry weight of the functional layer formulation.

5. The medical device according to claim 1, wherein the primer layer has a thickness of 0.1-20 μm, and the functional layer has a thickness of at least 0.1 μm, wherein the total dry thickness of the coating is 100 μm or less.

6. The medical device according to claim 1, wherein the medical device is selected from the group consisting of:

(a) catheters,
(b) endoscopes and laryngoscopes,
(c) tubes for feeding or drainage or endotracheal use,
(d) guide wires,
(e) condoms,
(f) barrier coatings for gloves, wound dressings, contact lenses, implants, or extracorporeal blood conduits, or
(g) membranes for dialysis, blood filters, or devices for circulatory assistance.

7. The medical device according to claim 1, wherein the primer layer formulation comprises:

(a) a supporting polymer selected from the group consisting of polyethers and polythioethers, including copolymers thereof, in a total concentration of 1-20 wt %, based on the total weight of the primer layer formulation;
(b) a Norrish I type photo-initiator in a total concentration 1-10 wt %, based on the weight of component (a); and
at least 68 wt % of a solvent, wherein the components (a) and (b) are dissolved or dispersed in the solvent.

8. The medical device according to claim 1, wherein the supporting polymer is a copolymer composed of one or more of a polyether or polythioether; a moiety comprising at least two isocyanates; or a hydroxyalkylacrylate, a hydroxyalkylmethacrylate, a polyhydroxyalkylacrylate or a polyhydroxymethacrylate.

9. The medical device according to claim 8, wherein the supporting polymer is a copolymer composed of one or more of polyalkylene glycols or polytetrahydrofuran; toluene diisocyanate or 4-cyclohexyldiisocyanate; or hydroxyethylacrylate or hydroxyethylmethacrylate.

10. The medical device according to claim 8, wherein the supporting polymer has a number average molecular weight in the range of 300-20,000 g/mol.

11. The medical device according to claim 1, wherein the primer layer formulation comprises an organic solvent.

12. The medical device according to claim 1, wherein:

(A) the multifunctional polymerizable compound according to formula (1) is present in a total concentration of –0.5-20 wt %, based on the total weight of the functional layer formulation; and (B) a photo-initiator is present in the functional layer formulation in a total concentration of 0.1-10 wt. based on the total weight of (A) and (C) in the functional layer formulation; and (C) a functional polymer is present in the functional layer formulation in a total concentration of 30 wt %, based on the total weight of the functional layer formulation; and a solvent is present in the functional layer formulation in an amount of at least 68 wt %, and wherein the components (A), (B), and optionally (C) are dissolved or dispersed in the solvent.

13. The medical device according to claim 12, wherein the functional layer formulation further comprises at least one surfactant (D).

14. The medical device according to claim 1, wherein a functional polymer (C) is present and is selected from the group consisting of poly(lactams), polyurethanes, homo- and copolymers of acrylic and methacrylic acid, polyvinyl alcohol, polyvinylethers, maleic anhydride based copolymers, polyesters, vinylamines, polyethylene imines, polyethyleneoxides, poly(carboxylic acids), polyamides, polyanhydrides, polyphosphazenes, cellulosics, heparin, dextran, polypeptides, polysacharrides, polyesters, and polypeptides.

15. The medical device according to claim 14, wherein the weight average molecular weight of the functional polymer (C) is in the range of 20,000 to 10,000,000 g/mol.

16. The medical device according to claim 1, wherein the medical device is a catheter.

17. The medical device according to claim 1, wherein G is chosen from the group consisting of polyethers, polyurethanes, polyepoxides, polyamides, polyacrylamides, poly(meth)acrylics, polyoxazolidones, polyvinyl alcohols, polyethylene imines, polypeptides and polysaccharides, or any combination of the above.

18. The medical device according to claim 1, wherein G is a polymer comprising at least one polyethylene glycol or polypropylene glycol block.

19. The medical device according to claim 1 wherein each $R_1$ and each $R_2$ independently represents a hydrogen or a C1-C20 hydrocarbon.

20. The medical device according to claim 1, wherein n is from 2 to 8.

21. The medical device according to claim 1, wherein n is 2 or 3.

* * * * *